US00PP29560P2

(12) United States Plant Patent
Osiecki

(10) Patent No.: US PP29,560 P2
(45) Date of Patent: Jul. 31, 2018

(54) ***SPATHIPHYLLUM* PLANT NAMED 'S48'**

(50) Latin Name: *Spathiphyllum hybrida*
Varietal Denomination: S48

(71) Applicant: Marian Osiecki, Marianna, FL (US)

(72) Inventor: Marian Osiecki, Marianna, FL (US)

(73) Assignee: Oglesby Plants International, Inc., Altha, FL (US)

( * ) Notice: Subject to any disclaimer, the term of this patent is extended or adjusted under 35 U.S.C. 154(b) by 0 days.

(21) Appl. No.: 15/530,471

(22) Filed: Jan. 19, 2017

(51) Int. Cl.
*A01H 5/02* (2018.01)

(52) U.S. Cl.
USPC ..... Plt./364

(58) Field of Classification Search
USPC ..... Plt./364
See application file for complete search history.

*Primary Examiner* — Annette H Para
(74) *Attorney, Agent, or Firm* — Cassandra Bright

(57) ABSTRACT

A new and distinct *Spathiphyllum* cultivar named 'S48' is disclosed, characterized by very dark green, glossy foliage, rapid growth and early production of secondary shoots. The new variety can be produced commercial in tightly spaced pots and maintains its very dark green color under higher light conditions or low nutrient levels. The new variety is commercially suitable for 20 and 25 cm pot production. The new variety is a *Spathiphyllum*, typically produced as an indoor ornamental plant.

3 Drawing Sheets

Latin name of the genus and species: *Spathiphyllum hybrida.*

Variety denomination: 'S48'.

BACKGROUND OF THE INVENTION

The new cultivar is a product of a planned breeding program. The objective of the breeding program was to develop new *Spathiphyllum* varieties suitable for production in commercial pot sizes of 20 to 25 cm, with fast growth, upright plant habit and dark green foliage. The new variety originated from a cross-pollination of a proprietary, unpatented seed parent referred to as '96-3-04' and the pollen parent, a proprietary, unpatented *Spathiphyllum* referred to as '95-1-8'. The crossing was made during March 2007.

The new variety was discovered by the inventor, Marian Osiecki in September 2008 in a group of seedlings resulting from the crossing. The new cultivar was found in a commercial greenhouse in Altha, Fla.

Asexual reproduction of the new cultivar 'S48' was first performed at a commercial laboratory in Altha, Fla. by tissue culture explants in May 2011. Subsequent propagation by tissue culture has shown that the unique features of this cultivar are stable and reproduced true to type.

SUMMARY OF THE INVENTION

The cultivar 'S48' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'S48.' These characteristics in combination distinguish 'S48' as a new and distinct *Spathiphyllum* cultivar:

1. Very dark green, broad foliage.
2. Early production of secondary foliage, resulting in a full plant growth earlier.
3. Rapid growth.
4. Maintains very dark green color under higher than normal light conditions, or low nutrient levels.
5. Very symmetrical plant.
6. Plant habit suitable for 20 to 25 cm commercial pots.
7. Plants can be produced commercial in tightly spaced pots.

PARENT COMPARISON

Plants of the new cultivar 'S48' are similar to the seed parent in most horticultural characteristics. The new variety, however, differs in the following:

1. The new variety has a smaller plant size. The height of 'S48' is 80-85 cm tall, the seed parent is 110-120 cm tall, the diameter of 'S48' is 95-100 cm, the seed parent diameter is 170 cm.
2. 'S48' has shorter leaf blade; 50-55 cm long whereas '96-3-04' has a leaf length of 60-65 cm.
3. 'S48' has narrower leaf blade; 26-30 cm whereas '96-3-04' has a leaf blade width of 38-40 cm.
4. Leaf petiole of 'S48' is shorter; 35-40 cm where leaf petioles of '96-3-04' are 50-54 cm long
5. 'S48' flowers earlier than the seed parent.
6. 'S48' produces more basal clumps than the seed parent.
7. Spathes of the new variety are smaller, 30-32 cm long compared with 43-45 cm long spathes of the seed parent.
8. 'S48' matures earlier, is suitable for 20-25 cm pots whereas '96-3-04' is suitable for 25 cm and larger pots.

Plants of the new cultivar 'S48' are similar to the pollen parent in most horticultural characteristics. Plants of the new variety however differ in the following:

1. S48' is shorter plant; 80-85 cm tall whereas '95-1-8' is 100-115 cm tall.
2. 'S48' produces basal shoots later and less abundantly(2-3 shoots) than '95-1-8'(5-6 shoots).

3. 'S48' is a more opened plant whereas '95-1-8' is a more dense plant.
4. Flowers of 'S48' are closer to the foliage, 10-15 cm above foliage whereas flowers of '95-1-8' are 25-30 cm above foliage.
5. The color of leaf blade of 'S48' is much darker than '95-1-8'.
6. The leaf blade of 'S48 is thicker than '95-1-8'.
7. The foliage of 'S48' is more upright than that of '95-1-8', which is horizontal.
8. The edges of the leaf blades of 'S48' are less wavy than those of '95-1-8'.
9. The leaf blade of 'S48' is longer; 50-55 cm compared to 40-44 cm of '95-1-8'.
10. The leaf blade of 'S48' is wider 26-30 cm compared 20-23 cm wide of '95-1-8'.
11. The leaf petiole of 'S48' is shorter; 35-40 cm whereas leaf petiole of '95-1-8' is 65-70 cm.
12. 'S48' flowers later and less abundantly than '95-1-8'.
13. Flowers of 'S48' are bigger 30-32 cm long whereas flowers of '95-1-8' are 23-25 cm long

COMMERCIAL COMPARISON

'S48' can be compared to compared to the commercial variety *Spathiphyllum* 'Gorgusis' U.S. Plant Pat. No. 6,964 Plants of 'Gorgusis" are similar to plants of 'S48' in most horticultural characteristics, however, plants of 'S48' differ in the following:

1. The new variety is shorter. 'S48' is 80-85 cm tall, whereas this comparator is 100-105 cm.
2. 'S48' is 95-100 cm wide whereas this comparator width is 115-120 cm.
3. 'S48' is a more dense plant whereas 'Gorgusis' is very open.
4. 'S48' has an upright growth habit whereas this comparator is more horizontal/cascading
5. S48 is suitable for production in 20 cm pots whereas this comparator must be produced in pots 25 cm and larger.
6. 'S48' branches earlier (develops later shoots) where Sensation does not branch.
7. Leaf blades of 'S48' are 5-10 cm shorter than leaf blades of this comparator.
8. Leaf petioles of 'S48' are 8-10 cm shorter than leaf petiole of this comparator.
9. The color of the midrib of 'S48' is lighter (Yellow Green 147B) than midrib of this comparator (Yellow Green 147A).
10. The veins of the leaf blade of 'S48' are deeper and spaced closer than veins of 'Gorgusis'.

BRIEF DESCRIPTION OF THE PHOTOGRAPHS

The accompanying photograph in FIG. 1 illustrates in full color a typical plant of 'S48' grown in a greenhouse in Altha, Fla. This plant is approximately 10 months old, shown in an 8 inch pot.

Figure 1:
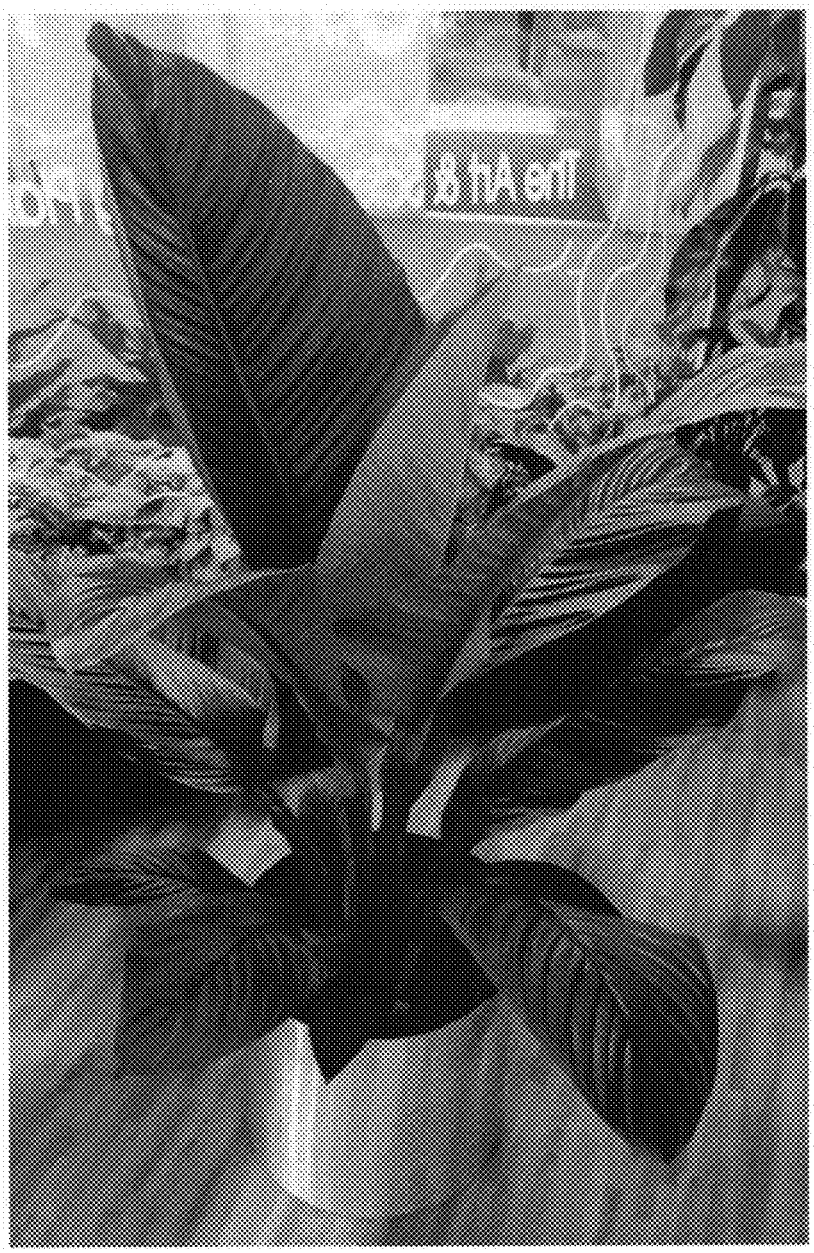
Figure 2:
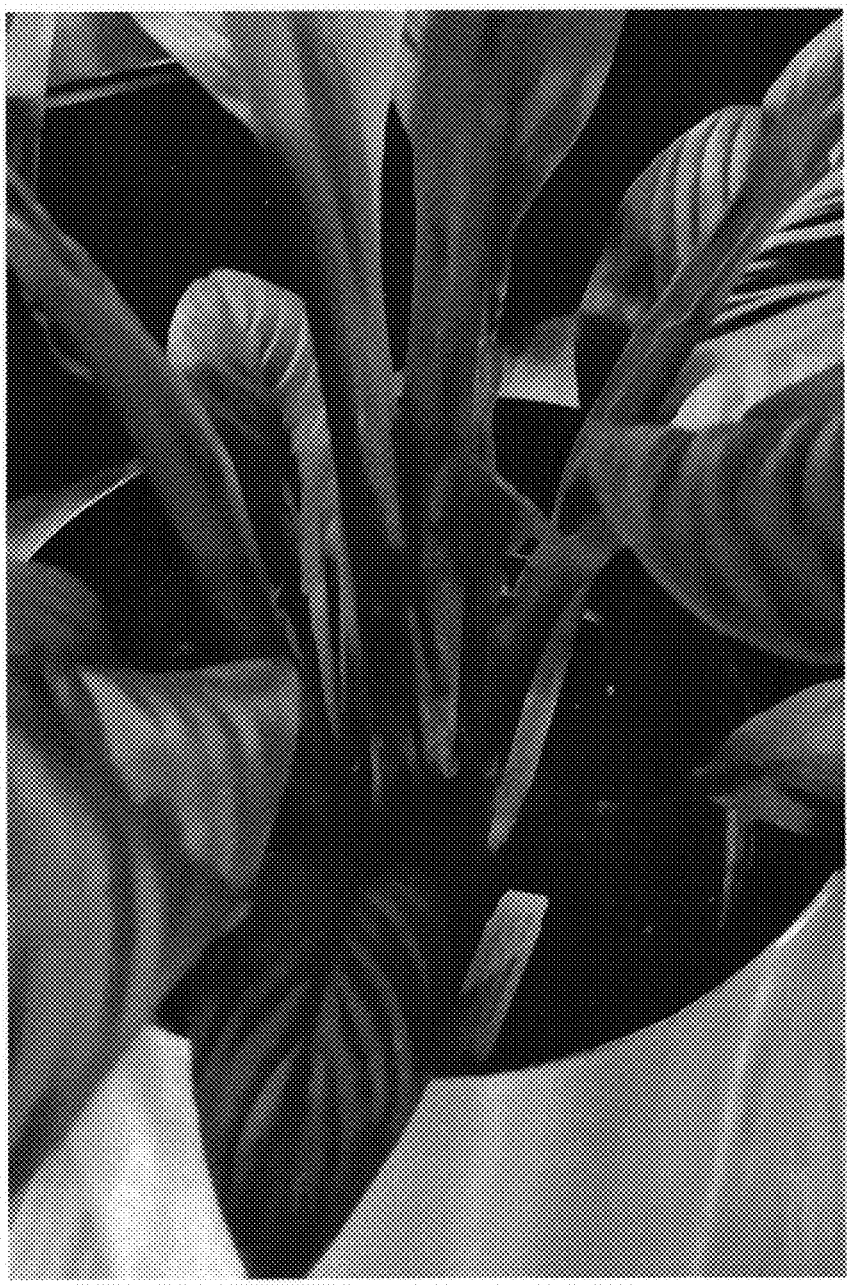
FIG. 2 illustrates a view of the strong late shoot production.
Figure 3:
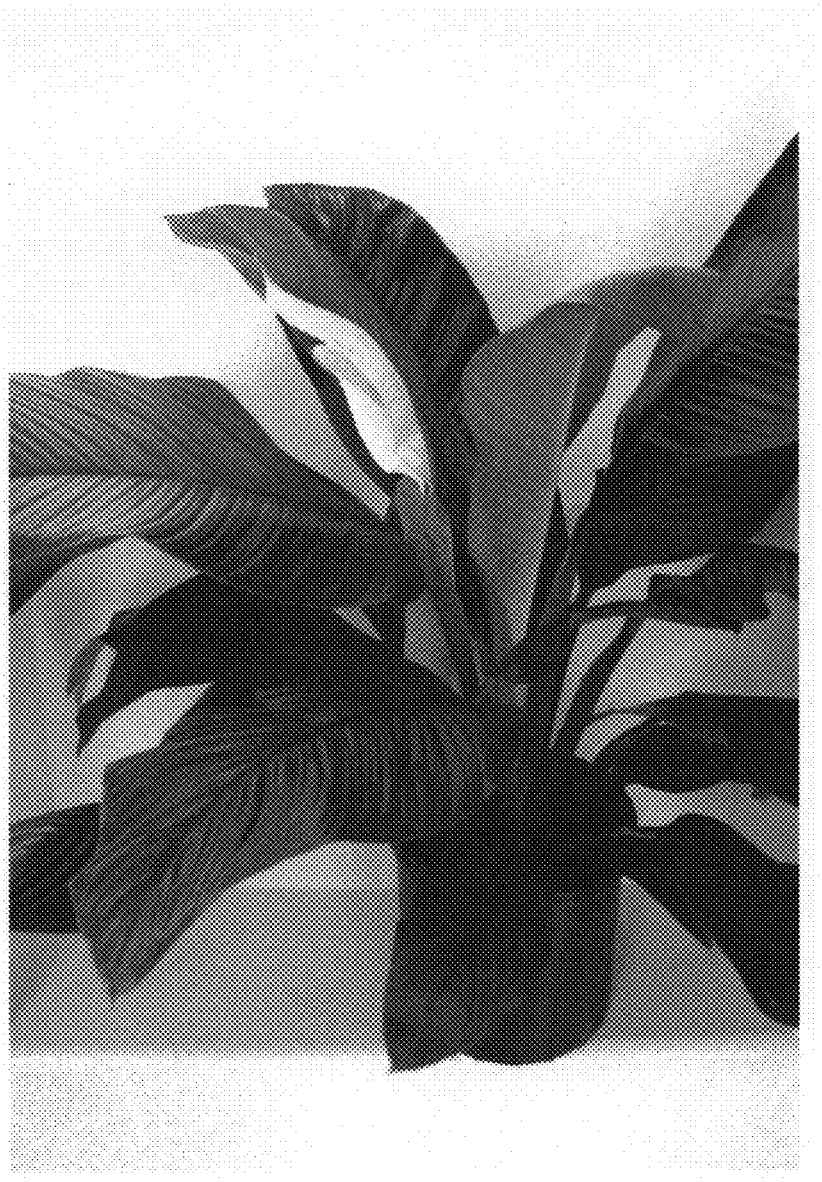
FIG. 3 illustrates a flowering plant in a 2 gallon pot, at approximately 14 months of age.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe a ten month old 'S48' plants grown in a climate controlled greenhouse in Altha, Fla., USA. Temperatures ranged from 20° C. to 25° C. at night to 25° C. to 32° C. during the day. No artificial light, photoperiodic treatments were given to the plants. Plants were grown in 80% shade, resulting in approximately 800 to 1200 foot candles of light. Measurements and numerical values represent averages of typical plant types.

Botanical classification: *Spathiphyllum hybrida* 'S48'.

PROPAGATION

Time to initiate roots: Approximately 18 days at approximately 25° C. soil temperature.

Time to produce a fully rooted plantlet: Approximately 14 weeks at approximately 20 to 30° C. soil temperature.

Root description: Thick, fleshy roots with fine, fibrous lateral roots. Color near Orange-White 158D.

PLANT

Growth habit: Rapid, upright.

Plant shape: Upright, leaves only slightly arching out.

Height: Approximately 80 to 85 cm.

Plant spread: Approximately 95 to 100.

Pot size of plant described: 10 inch.

Growth rate: Moderate.

Number of clumps of leaves: 2 to 3 then an additional 2 to 3 clumps when mature.

Number of leaves per clump: Average 6.

Number of leaves per plant: Approximately 20 to 35.

Age of plant described: Approximately 10 months.

FOLIAGE

Leaf:

*Arrangement*.—Single leaves emerging basally.

*Average length* (*excluding petiole*).—Approximately 50 to 55 cm.

*Average width*.—Approximately 26 to 30 cm.

*Shape of blade*.—Broad elliptic.

*Aspect*.—Very slightly undulating, upward fold from mid-vein and slightly recurved overall.

*Apex*.—Apiculate. Apiculation approximately 1 cm.

*Base*.—Attenuate.

*Margin*.—Entire.

*Appearance*.—Glossy upper surface. Matte lower surface.

*Texture of top surface*.—Glabrous, wrinkled from veins.

*Texture of bottom surface*.—Glabrous.

*Color*.—Young foliage upper side: Near Green 139A. Young foliage under side: Near Green 137B. Mature foliage upper side: Near Green 139A, but darker. Mature foliage under side: Near Green N 138B.

Venation:
*Type*.—Pinnate.
*Venation coloration upper side*.—Near Green 139A.
*Venation coloration under side*.—Near Yellow-Green 144B.
Petiole:
*Length*.—Approximate range between 35 and 40 cm.
*Width*.—At geniculum: Approximately 0.9 cm. Above clump: Approximately 1.4 cm.
*Color*.—Near RHS Green 137A.
*Strength*.—Very strong.
*Other*.—Petiole wing present.
Geniculum:
*Length*.—Approximately 6.5 cm.
*Width*.—Approximately 1.4 cm.
*Color*.—Near RHS Green 137B.
Petiole wing/petiole sheath:
*Length*.—Approximately same length as individual petiole, becoming approximately 1 cm longer with age.
*Width*.—Approximately 0.6 cm.
*Color*.—Near RHS Green 137A.

INFLORESCENCE

Arrangement: Spathes with spadices held just above the foliage on erect peduncles arising from the petiole sheath.
Flowering habit: Continuous.
Quantity of spathes per plant: On average 1 or 2 fully open spathes in good condition.
Natural flowering season: Autumn to Winter.
Time to flowering: 10 weeks after standard Gibberellic acid treatment of 200 ppm.
Fragrance: None.
Self-cleaning or persistent: Persistent.
Flower longevity: Flowers stay in good condition approximately 5 weeks on the plant.
Spathe:
*Aspect*.—Cupped.
*Length*.—Approximately 30 to 32 cm.
*Width*.—Approximately 10 cm.
*Shape*.—Elliptic.
*Margin*.—Entire.
*Apex*.—Cirrose.
*Base*.—Cuneate, symmetrical.
*Color*.—Front when opening: Near RHS White 155C. Mid-vein near Green 143C, flush near mid-vein near Yellow-Green 144B. Back when opening: Near RHS White 155C. Mid-vein near Green 143C, flush near mid-vein near Yellow-Green N144B. Front when mature: Near RHS White 155C. Mid-vein near Green 143A, faint flush near mid-vein near Yellow-Green N144B. Back when mature: Near RHS White 155C. Mid-vein near Green 143A, flush near mid-vein near Yellow-Green N144C. Front Fading to: Near RHS White 155C. Mid-vein Green 143C, flush near N144D. Back Fading to: Near RHS White 155C. Mid-vein Green 143C, flush near N144B.
Spadix:
*Shape*.—Columnar, arising from the top of the peduncle.
*Tip*.—Obtuse.
*Base*.—Obtuse.
*Length*.—Approximately 15 cm.
*Width*.—Approximately 2 cm.
*Color*.—When opening: Near RHS White 155C. Mature: Near RHS White 155A.
*Quantity of flowers per spadix*.—Approximately 450.
*Spadix flower arrangement*.—Bisexual, rounded.
*Spadix flower diameter*.—Approximately 0.2 cm.
*Spadix flower depth*.—Approximately 0.3 cm.
Peduncle:
*Length*.—Approximately 60 cm, measured from base, which emerges from leaf axil.
*Width*.—Approximately 0.9 cm.
*Color*.—Near RHS Green 141A.
*Strength*.—Very strong.

REPRODUCTIVE ORGANS

All flower parts and reproductive organs are highly reduced, to the point of immeasurable.
Quantity of pollen: Abundant.
Pollen color: Near RHS White 155A.

OTHER CHARACTERISTICS

Disease resistance: Neither resistance nor susceptibility to normal diseases of *Spathiphyllum* have been observed.
Drought tolerance and cold tolerance: The new cultivar is a typical *Spathiphyllum*, cold tolerant to approximately 5 to 7° C. and does not tolerate drought.
Fruit/seed production: Not observed.

What is claimed is:

1. A new and distinct cultivar of *Spathiphyllum* plant named 'S48' as herein illustrated and described.

* * * * *